(12) United States Patent
Bach

(10) Patent No.: US 8,207,393 B2
(45) Date of Patent: Jun. 26, 2012

(54) FOAMED PRESSURE SENSITIVE ADHESIVE BODY COMPRISING HYDROCOLLOIDS

(75) Inventor: Anders Bach, Copenhagen S (DK)

(73) Assignee: Coloplast A/S, Humlebaek (DK)

( * ) Notice: Subject to any disclaimer, the term of this patent is extended or adjusted under 35 U.S.C. 154(b) by 811 days.

(21) Appl. No.: 12/223,586

(22) PCT Filed: Feb. 15, 2007

(86) PCT No.: PCT/DK2007/050022
§ 371 (c)(1),
(2), (4) Date: Aug. 4, 2008

(87) PCT Pub. No.: WO2007/093186
PCT Pub. Date: Aug. 23, 2007

(65) Prior Publication Data
US 2009/0030361 A1    Jan. 29, 2009

(30) Foreign Application Priority Data
Feb. 17, 2006    (DK) .................................. 200600225

(51) Int. Cl.
*A61F 13/00* (2006.01)
(52) U.S. Cl. ................. 602/54; 602/41; 602/42; 602/46
(58) Field of Classification Search ............. 602/41–42, 602/48, 58, 46, 52; 604/344, 338, 341
See application file for complete search history.

(56) References Cited

U.S. PATENT DOCUMENTS

| | | | |
|---|---|---|---|
| 4,231,369 A | 11/1980 | Sorensen et al. | |
| 4,427,737 A | 1/1984 | Cilento et al. | |
| 4,551,490 A | 11/1985 | Doyle et al. | |
| 4,775,374 A | 10/1988 | Cilento et al. | |
| 4,867,748 A | 9/1989 | Samuelsen | |
| 5,006,401 A | 4/1991 | Frank | |
| 5,133,821 A | 7/1992 | Jensen | |
| 5,587,237 A | 12/1996 | Korpman et al. | |
| 5,643,187 A | 7/1997 | Naestoft et al. | |
| 6,180,544 B1 | 1/2001 | Jauchen et al. | |
| 6,326,524 B1 | 12/2001 | Fattman et al. | |
| 6,812,170 B1 | 11/2004 | Himmelsbach et al. | |

FOREIGN PATENT DOCUMENTS

| | | |
|---|---|---|
| EP | 0264299 A2 | 4/1988 |
| EP | 1007597 A1 | 6/2000 |
| EP | 1021494 A1 | 7/2000 |
| EP | 1086189 A1 | 3/2001 |
| GB | 2300195 A | 10/1996 |
| WO | WO9724093 A1 | 7/1997 |
| WO | WO9817212 A1 | 4/1998 |
| WO | WO9954422 A1 | 10/1999 |
| WO | WO0206687 A1 | 1/2002 |
| WO | WO2004080498 A1 | 9/2004 |

OTHER PUBLICATIONS

Bird et al., "Dynamics of Polymeric Liquids", vol. I, Fluid Mechanics, $2^{nd}$ Edition, 1987, pp. 113-117. Handbook of Pressure Sensitive Adhesive Technology, $2^{nd}$ Ed., Satas, Editor (Von Nostrand Reinhold, NY 1989).

*Primary Examiner* — Kim M Lewis
(74) *Attorney, Agent, or Firm* — Jacobson Holman PLLC

(57) ABSTRACT

The invention relates to an absorbent adhesive body of a foamed pressure sensitive hydrocolloid adhesive comprising one or more water soluble or water swellable hydrocolloids and having gas bubbles incorporated therein, where the gas in the gas bubbles are in direct contact with the pressure sensitive hydrocolloid adhesive and where tan δ for the adhesive in un-foamed form is below 0.35 at 40° C. and 0.001 rad/sec.

19 Claims, 1 Drawing Sheet

FOAMED PRESSURE SENSITIVE ADHESIVE BODY COMPRISING HYDROCOLLOIDS

This is a national stage of PCT/DK2007/050022 filed Feb. 15, 2007 and published in English.

FIELD OF THE INVENTION

The invention relates to an adhesive body of a foamed closed celled pressure sensitive hydrocolloid adhesive useful for medical applications, such as for wound dressings, ostomy appliances etc.

BACKGROUND OF THE INVENTION

Hydrocolloid adhesives for skin applications are well known in the art.

Hydrocolloid adhesives for skin applications have attractive features in terms of moisture absorption and price. However, hydrocolloid adhesives tend to be rough on the skin, and when such adhesives are removed from the skin, the skin may be stripped of its upper layer. Changing the adhesive repeatedly as would be the case for e.g. ostomy appliances leaves the skin damaged and severe pain may be associated with the removal of the adhesives. The problem can to some extent be handled by using softer adhesives that deforms more during peeling. When the deformation is larger, the area over which the peel force is transmitted to the skin becomes broader leaving the skin less stressed compared to a harder adhesive with the same peel force. On the other hand, increasing the softness of the adhesive by modifying the chemical composition thereof may reduce the structural integrity of the adhesive and the adhesive may fail cohesively.

It has now been found that a larger deformation of the same adhesive when peeling with the same peel force may be achieved by eliminating or reducing the incompressibility restriction imposed by the solid adhesive by introducing small bubbles of gas that are able to expand when internal pressure reduces because of peel deformation of the adhesive mass.

In this way, the adhesive mass is still incompressible in a differential fluid element but in a local scale of the size of the included bubbles, the adhesive mass is compressible and able to expand with the given flow.

Introduction of bubbles into an adhesive lowers the modulus of the adhesive and makes it softer and more flexible. An adhesive comprising bubbles will have a lower bending resistance than its incompressible counterpart. This will improve wear comfort.

A foamed adhesive is also more impact resistant and has a cushioning effect, because a soft foamed adhesive is able to distribute loads better and improve pressure relief.

A disadvantage of the observed in a foamed adhesive is that surface tension tends to merge bubbles together, leading to larger bubbles. The density may also increase if bubbles merge with the surface of the adhesive.

Porous or foamed hydrocolloid adhesives for medical applications have already been described in the art.

Thus, U.S. Pat. No. 4,775,374 describes a skin barrier for use by ostomates. The barrier makes use of a porous layer of hydrocolloid adhesive with holes or pores having a size 10-300 µm. The foamed adhesive layer is thin compared to the bubble size 1-10 mils (corresponding to 25.4-254 µm) and this construction creates open pores for gas transport through the adhesive layer. The gas transport in these adhesives should be within 1-100 $cm^3/sec/in^2$ according to ASTM D-726-71.

The foamed adhesive body of the present invention differs from the adhesives described in U.S. Pat. No. 4,775,374 in that the foam is closed celled and without interpenetrating cavity structure. Furthermore, the average cell diameter of the gas bubbles in the adhesive body of the invention is limited to a narrow range of diameters providing the necessary compressibility.

U.S. Pat. No. 6,326,524 describe foamed hydrocolloid adhesives with a bubble size of 200-4000 µm. It is said that the foamed structure of the adhesive improves absorbency, enables transmission of moisture through the adhesive, increases flexibility and lowers product cost. The bubble size is limited to be in the regime 200-4000 µm. The adhesive used in the example has been tested and was found to be very hard.

The foamed adhesive body of the present invention differ from the adhesives described in U.S. Pat. No. 6,326,524 in that the average diameter of the gas bubbles in the adhesive of the present invention is much smaller and the adhesive body is considerably softer which provides the desired broad peel front. Large bubble diameters may compromise cohesion of the adhesive body during peeling.

WO 2004/080498 also suggests absorbent polymer compositions in the form of foams of a pressures sensitive hydrocolloid adhesive. There is no information as regards the average diameter of the gas bubbles in these materials.

The foamed adhesive body of the present invention differs from the adhesives described in WO 2004/080498 in that the bubbles in WO 2004/080498 is created using expandable microspheres. These bubbles are hard as they are incapsulated in a hard material even after expansion. Thus, such an adhesive would not provide the necessary compressibility described in this patent.

SUMMARY OF THE INVENTION

The present invention relates to an absorbent adhesive body of a foamed pressure sensitive hydrocolloid adhesive comprising one or more water soluble or water swellable hydrocolloids and having gas bubbles incorporated therein, where the gas in the gas bubbles are in direct contact with said pressure sensitive hydrocolloid adhesive and where the tan δ for said adhesive in un-foamed adhesive is below 0.35 at 40° C. and 0.001 rad/sec.

In particular the present invention relates to an absorbent adhesive body as above having gas bubbles incorporated in the pressure sensitive hydrocolloid adhesive having an average bubble diameter between 20-80 µm.

The invention also relates to the use of the above-mentioned adhesive body for various medical applications, such as for attachment of medical devices to the skin, as a dressing or bandage e.g. for wounds, and for attachment of ostomy appliances to the skin.

DETAILED DESCRIPTION OF THE INVENTION

Figure 1:
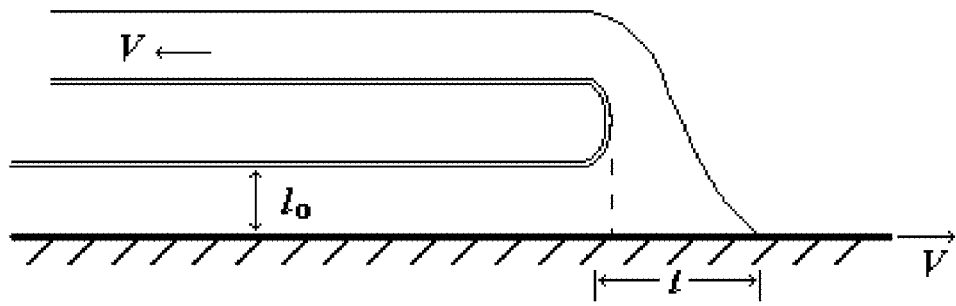
FIG. 1 shows a schematic drawing of an experimental apparatus for filming a peel front in a microscope.

This invention relates to a foamed adhesive body suitable for various medical applications, in particular within the field of incontinence, wound care and ostomy care.

In order to achieve long-term stability of the bubbles it is necessary to control the elastic and plastic properties of the adhesive. For a foamed adhesive to remain stable, the adhesive needs to be elastic at long timescales. On the other hand, if the adhesive is too elastic, it will no longer be sufficiently adhesive since it is the ability of an adhesive to 'flow' to a surface that makes it a good adhesive. Therefore, when formulating a foamed hydrocolloid adhesive, it is necessary to have as high a degree of plasticity at long timescales as possible without the degree of plasticity being so high that the foamed adhesive is no longer stable.

The parameter tan δ as defined in "Dynamics of polymeric liquids", Vol 1, sec ed 1987, Bird, Armstrong and Hassager, John Wiley and Sons inc., may be used as a measure of the elastic and plastic properties of an adhesive. A tan δ=0 corresponds to an ideal elastic material and tan δ->∞ corresponds to an ideal liquid. In the definition of tan δ, δ is a function of frequency where small frequencies correspond to long time scales. Thus, tan δ at low frequencies provides a measure for the elastic/plastic relationship at large timescales. For the adhesive to be stable, tan δ should be small. However, to act as an adhesive tan δ should be relatively high.

It has been found, that hydrocolloid adhesives having a tan δ for the hydrocolloid adhesive in un-foamed form, which is below 0.35, preferably below 0.30 at 40° C. and 0.001 rad/sec provides a foamed adhesive with good stability and sufficient adhesive properties.

Tan δ at 40° C. and 0.001 rad/sec may be measured as follows: A plate of the un-foamed adhesive material was pressed into a plate of 1 mm thickness. A round sample of 25 mm in diameter was cut out and placed in a RheoStress RS600 rheometer from Thermo Electron. The geometry applied was parallel plates 25 mm and the deformation was fixed at 1% to ensure that measurements were in the linear regime. The measurement was carried out at 40° C.

In one preferred embodiment, the present invention relates to an adhesive body of a foamed closed celled pressure sensitive hydrocolloid adhesive wherein the average bubble diameter is between 20-80 µm. In a preferred embodiment of the invention the average bubble diameter is 30-70 µm.

According to another preferred embodiment of the invention, at least 95% of the bubbles have a bubble diameter between 10 and 150 µm.

"Average bubble diameter" means the number average bubble diameter determined using a microscope mounted with a digital camera. According to the invention, the average bubble diameter is measured by recording pictures of the foamed adhesive body and measuring the bubble diameter by comparing with microscopy pictures of an objective micrometer.

This method also allows for the determination of the percentage of bubbles with a diameter within a given range, e.g. a diameter between 10 and 150 µm.

Varying the foaming conditions may be used to control the diameter of the bubbles and a person skilled in the art may determine the suitable foaming conditions. The foaming procedures are described in more detail below.

The pressure sensitive hydrocolloid adhesive used for the formation of the foamed adhesive body should in itself be relatively soft.

Thus, the pressure sensitive hydrocolloid adhesive composition used for the preparation of the foamed adhesive body of the invention is preferably a soft pressure sensitive hydrocolloid adhesive, suitably an adhesive having a complex modulus below 80 KPa at 1 rad/s at 32° C., or even more preferred below 60 KPa at 1 rad/s at 32° C. The complex modulus is defined in "Dynamics of polymeric liquids", Vol 1, sec ed 1987, Bird, Armstrong and Hassager, John Wiley and Sons inc.

On the other hand, the pressure sensitive hydrocolloid containing adhesive mass used for the preparation of the foamed adhesive body of the invention should not be too soft as this may compromise the cohesion of the adhesive layer causing the adhesive body to leave residues on the skin.

The above-mentioned value for the complex modulus, is the value obtained by measuring the complex modulus on the unfoamed pressure sensitive hydrocolloid adhesive using the method described below.

A plate of the un-foamed material was pressed into a plate of 1 mm thickness. A round sample of 25 mm in diameter was cut out and placed in a RheoStress RS600 rheometer from Thermo Electron. The geometry applied was parallel circular plates 25 mm and deformation was fixed at 1% to ensure that measurements were in the linear regime. The measurement was carried out at 32° C.

The pressure sensitive hydrocolloid adhesive may be based on any known adhesive mass useful for skin application. A number of pressure sensitive adhesives may be useful as starting material for the foamed adhesive bodies according to the invention, see for example the adhesive compositions disclosed in U.S. Pat. No. 4,551,490, EP 1 021 494 B1, GB 2 300 195, U.S. Pat. No. 4,231,369, U.S. Pat. No. 5,006,401, EP 1 007 597 B1, EP 1 086 189, WO 98/17212, U.S. Pat. No. 5,587,237, WO 02/06687 and U.S. Pat. No. 4,775,374.

The pressure sensitive hydrocolloid adhesive used for the preparation of the foamed adhesive body of the invention, is an adhesive having a suitable softness, see the values given for the modulus above and tan δ as described above.

The hydrocolloid adhesive used for the preparation of the foamed adhesive body of the invention could be any type of hydrocolloid adhesive useful for skin applications. In Handbook of Pressure Sensitive Adhesive Technology $2^{nd}$ ed., Satas, editor, (Von Nostrand Reinhold, New York 1989) a number of useful pressure sensitive adhesives are discussed: A-B-A block copolymer adhesives, amorphous poly alfa olefins, natural rubbers, polyisoprene, butyl rubber, polyisobutylene, silicones, polychlorophrene, acrylic adhesives and acrylic dispersions and polyvinylethers. Any of these pressure sensitive adhesives, or blends thereof, may be used to produce hydrocolloid adhesives which may be used to prepared the foamed adhesive bodies of the invention.

According to a preferred embodiment, the adhesive composition used for the preparation of the foamed adhesive body of the invention comprises a cross-linked polyalkyleneoxide polymer, preferably a polypropyleneoxide polymer.

According to another preferred embodiment, the adhesive composition used for the preparation of the foamed adhesive body of the invention comprises one or more polyisobutylenes, a tri block copolymer, a low molecular weight diblock copolymer, a tackifier, mineral oil and one or more water soluble or water swellable hydrocolloids.

The polyisobutylenes is typically present in an amount from 0% to 50% w/w and suitably has molecular weight between 40 000 and 800 000. Polyisobutylene is added in order to increase tack and adhesion the skin. Such polyisobutylenes are commercially available under the trademark Oppanol from BASF.

The block-copolymer is typically a styrene block copolymer (e.g. a SIS, SBS or SEBS tri block copolymer containing a certain amount of diblock copolymer) and it is present in an amount from 5 to 40% w/w. Suitable products are commercially available Kraton polymers under the trademark Kraton, or from Nippon Zeon Co., Ltd. under the trademark Quintack.

In WO 99/54422 it is described how the use of diblock copolymers, such as SI and SB block copolymers in the adhesive composition may increase the softness and plasticity of the adhesive.

The low molecular weight diblock copolymer is suitably present in an amount from 0 to 30% w/w. Suitable di-block polymers are commercially available from Kuraray under the trademark LIR.

The tackifier is suitably present in an amount from 0 to 50% w/w. Suitable tackifiers may be Arkon P70, Arkon P90, Arkon P115 from Arkawa chemical industries or Regalite R91 or Foral 85 from Eastman.

The mineral oil is suitably present in an amount from 0-40% w/w. A suitable mineral oil is Parafluid PL50 from Parafluid Mineraloelgesellschaft mbH.

In general the softness of these known pressure sensitive hydrocolloid adhesives may be improved by regulating the amount of e.g. mineral oil and plasticizer.

The water soluble or water swellable hydrocolloids are suitable present in an amount above 20% w/w. Preferably the amount of hydrocolloid is between 30 and 60% w/w. Suitably the water soluble or water swellable hydrocolloids are selected from natural or synthetic hydrocolloids, such as guar gum, locust bean gum, pectin, alginates, gelatine, xantan or gum karaya, cellulose derivatives, (e.g. salts of carboxymethyl cellulose such as sodium carboxymethyl cellulose, methyl cellulose and hydroxypropyl cellulose) sodium starch glycolate, polyvinylalcohol and polyethylene glycol. Suitable hydrocolloids are e.g. AQ 1045 (a branched water dispersible polyester) from Eastman, Pectin LM 12CG Z or Pectin USP/100 from Copenhagen Pectin, Natrosol (hydroxyethyl cellulose, non-ionic, water soluble ethers of cellulose and ethylene oxide) produced by AQUALON, Blanose 9H4XF (carboxymethyl cellulose) available from Hercules, Akucell® AF 2881 (carboxymethyl cellulose) available from Akzo, AquaSorb® (crosslinked carboxymethyl cellulose) from Aqualon, Sorbalg pH 470 (Calcium alginate) from Danisco Ingredients, Denmark.

The hydrocolloids may also be selected from microcolloids (e.g having a particle size less than 20 microns or preferably below 5 or 2 microns), such as those described in WO 02/06687.

A suitable hydrocolloid adhesive composition for the preparation of the foamed adhesive body of the invention comprises:

0%-50% w/w of polyisobutylenes,

5%-40% w/w of a triblock copolymer comprising a certain amount of diblock copolymer, 0%-30% w/w of a low molecular weight diblock copolymer, 0%-50% w/w of a tackifier, 0%-40% w/w mineral oil and above 20% w/w one or more water soluble or water swellable hydrocolloids.

The adhesive compositions may optionally comprise further components normally used in of adhesive compositions e.g. pigments such as zinc oxide or titanium dioxide, antioxidants etc. The compositions may optionally comprise minor amounts of conventional plasticizers if special properties are desired.

For some purposes it is suitable also to include smaller amounts of a filler in the mass of the invention which may add to the cohesion and also contribute to the plasticity. Such filler may e.g. be any filler known per se for ostomy or wound care purposes such as talc, calcium carbonate, china clay, zinc oxide or the like. Such filler may constitute up to 20% by weight of the composition.

Still further, the adhesive may optionally comprise further constituents such as emollients, disinfecting agents and/or bactericidal agents known per se for use for ostomy or wound care purposes.

Several methods for introducing gas bubbles into an adhesive have been described.

Chemical blowing agents or other materials added to the adhesive formula itself may generate gas bubbles by a variety of mechanisms. These mechanisms include but are not limited to chemical reaction, physical changes, thermal decomposition or chemical degradation, leaching of a dispersed phase, volatilization of low boiling materials or by a combination of these methods.

Any of the commercially known chemical blowing agents may be used. The chemical blowing agents is suitably non-toxic, skin friendly, and environmentally safe, both before and after decomposition.

The term chemical blowing agent is used herein to cover the use of single or multiple component chemicals in a mixture or paste. Suitable chemical blowing agents include the carbonates, such as ammonium carbonate, ammonium bicarbonate, sodium carbonate, sodium bicarbonate, and calcium carbonate. Improved gas generation may be achieved by using a mixture of carbonates as above and various organic acids including, but not limited to, stearic, oleic, phthalic, maleic, citric, tartaric acid, and abietic acids. An excess of organic acids are preferably added to the carbonates of alkali metals, so the final reaction products have an acidic character.

The amount of chemical blowing agent to be added to hydrocolloid adhesive may suitably range from about 1% up to about 20% by weight. The amount of gas to be added may be determined by measuring the amount of gas generated from a candidate mixture and calculating the amount of foaming required for the final product, tempered by experience of the amount of gas lost to atmosphere during the foaming process. The creation of gas bubbles in an adhesive mass by a chemical blowing agent is described in more detail in U.S. Pat. No. 6,326,524.

Another method for creating a foamed hydrocolloid adhesive is a method where a mechanical process is used to add a physical blowing agent, similar to whipping the adhesive mass into froth, thus creating a foamed structure. Many processes are possible including processes involving incorporation of atmospheric air, nitrogen, carbon dioxide, or other gases or low boiling point volatile liquids during the compounding, extrusion, converting processes or other manufacturing processes for the adhesive.

The pressure sensitive hydrocolloid adhesive may for example be foamed by mixing the adhesive mass with a gas (air, nitrogen, carbon dioxide, or other gases), or low boiling point volatile liquids at a temperature above the melting point of the adhesive at an elevated pressure (e.g. around 50 bar). The high pressure causes the gas to be dissolved in the molten adhesive mass. When the pressure is relieved, the gas starts to flash out of the adhesive mass, which is supersaturated with gas, both by expansion in un-dissolved bubbles and by forming new bubbles. The mixture may then be fed through a die or extruder onto a release liner.

The creation of gas bubbles in a pressure sensitive hydrocolloid adhesive may also be achieved by the method described in U.S. Pat. No. 4,775,374 where the components of the pressure sensitive hydrocolloid adhesive is dispersed in a hydrocarbon solvent such as heptane, or hexane or mixtures thereof, followed by deposition of a thick layer, for example by means of a knife-over-roller, of the slurry on a release liner. The slurry deposited on the release liner is then dried, for example by passing through a drying tunnel, to achieve a low level of residual hydrocarbon solvent in the adhesive. The temperature and the time passed in the drying zone is controlled so that numerous small gas bubbles are generated from the solvent evaporation.

The adhesive mass containing the chemical or physical blowing agent can be processed into foam under any of the techniques described above. Processing includes forming the adhesive mass into sheet, either flat or contoured, by extrusion, by pressing, by injection molding, or by thermoforming or by any other typical adhesive processing method.

Cutting of the adhesive sheet for a wound dressing or an ostomy wafer or any other typical shape may be performed either before or after the foaming of the adhesive mass, depending on the foaming method used. Suitably, the adhesive mass is foamed during the extrusion process, followed by calendaring, lamination, and cutting of the foamed sheet into a specific product.

A person skilled in the art will be able to select the appropriate conditions for the process for creation of a foamed adhesive body having an average bubble size diameter and a bubble size distribution according to the invention.

Preferably, the foaming method and the foaming conditions is selected so that the density of the foamed pressure sensitive hydrocolloid adhesive is below <0.9 times the density of the same un-foamed adhesive.

According to a particular embodiment of the invention, more than 90% of the bubbles in the absorbent adhesive body are closed celled, which is an advantage when the adhesive body is used to encapsulate bodily fluids such as wound exudates or other fluids form the body.

In one aspect, the invention relates to a medical dressing comprising a foamed adhesive body of the invention. Such dressings include wound dressings, burn dressings, blister dressings, fistula dressings and dressings or bandages having a cushioning effect.

A dressing or bandage comprising an adhesive body of the invention usually comprises a backing film or layer on one surface thereof: The surface of the dressing or bandage, which is to be attached to the skin may be provided with one or more release liner(s).

Thus, in one embodiment of the invention, the dressing or bandage comprising an adhesive body of the invention is a layered product comprising the adhesive body between a backing layer and a release liner(s). The invention also relates to such a dressing or bandage where the release liner is absent.

The backing layer may be a water impervious layer or film which may be of any suitable material known per se for use in the preparation of wound dressings e.g. a foam, a woven or a non-woven layer, a film, such as a polyurethane-, polyethylene-, polyester- or polyimide film, or a film with multiple film layers. Suitably the backing layer is permeable to water vapor. Using a layer or film having a low modulus will also allow an easy application.

A suitable material for use as a water impervious film is a polyurethane. A preferred low friction film material is disclosed in U.S. Pat. No. 5,643,187. A suitable thickness of this film is below 20 microns. A thickness of about 12-18 microns is preferred for use with dressings according to the invention, because it results in a significant decrease of the modulus, compared to a film that is normally used when preparing medical dressings.

The water impervious layer or film is preferably a low-friction flexible polymer film reducing the risk of unwanted stress in the area of e.g. a crack or wound impeding the healing of such injury on a very exposed site such as the tip of a finger or toe.

The adhesive body and the dressing of the invention preferably has beveled edges in order to reduce the risk of "rolling-up" of the edges thereof and thereby reducing the wear-time and thus disturbing and prolonging the healing of cracks normally healing slowly on tips of fingers or toes due to physical stress. A beveling may be carried out discontinuously or continuously in a manner known per se e.g. as disclosed in EP patent No. 0 264 299 or U.S. Pat. No. 5,133,821.

The adhesive body, or the dressing of the invention may thus be a layer with a uniform thickness and optionally a beveled peripheral portion, or the adhesive body or dressing may be a body which is thickest in the central portion and gradually becomes thinner towards the peripheral edge. Bandages with beveled peripheral edges are well known in the art, see e.g. U.S. Pat. No. 4,867,748.

A release liner may for instance be siliconized paper. The release liner need not have the same contour as the dressing, e.g. a number of dressings may be attached to a larger sheet of release liner. The release liner is not present during the use of the dressing of the invention. Suitably, the release liner may be removed before or during application of the dressing.

The dressing of the invention may comprise a "non touch" grip known per se for applying the dressing to the skin without touching the adhesive layer. Such a non-touch grip is suitably formed by the release liner(s) and is not present after application of the dressing.

In another aspect, the invention relates to an ostomy appliance comprising an adhesive wafer or base plate comprising an adhesive body of the invention.

An ostomy appliance of the invention may be in the form of a base plate or wafer forming part of a two-piece appliance or in the form of a one-piece appliance comprising a collecting bag for collecting the material emerging from the stoma. A separate collecting bag may be attached to the base plate or wafer by any manner known per se, e.g. through mechanical coupling using a coupling ring or through the use of adhesive flanges.

An ostomy appliance of the invention also typically comprises a water impervious backing layer or film, an adhesive body of the invention and a release liner as discussed above.

An ostomy appliance of the invention may be produced in a manner known per se from materials conventionally used for the preparation of ostomy appliances.

The adhesive body of the invention may also be used in connection with incontinence devices, e.g. for attaching such devices to the skin or as adhesive strips for securing a urisheath during use.

EXPERIMENTAL PART

List of Materials:
Oppanol B30 from BASF (polyisobutylene)
Kraton 1163 (SIS/SI block copolymer) from Kraton Polymers.
Kraton LVSI 101 (from Low molecular weight SI copolymer) from Kuraray.
Arkon P90: A saturated alicyclic hydrocarbon resin from Arakawa Chemical Industries.
Paraffin oil, PL 500 from Parafluid Mineraloelgesellschaft mbH.
Blanose (carboxymethyl cellulose) from Hercules.
Aquasorb A800 (cross-linked carboxymentyl cellulose) from Hercules.
Kraton 1161 (SIS/SI block copolymer) from Kraton Polymers.
Arkon P115: A saturated alicyclic hydrocarbon resin from Arakawa Chemical Industries.

DOA oil (from Cognis performace chemicals, ltd)
Potato starch M4 (from KMC Amba.)
Antioxidant Lowinox (From Great lakes chemicals)

Example 1

A soft compressible HC adhesive layer was produced as follows:

Step 1. Preparing the Adhesive Mass

A mass of incompressible HC adhesive was prepared consisting of the ingredients listed in the table below

TABLE 1

| Polyisobutylene | 10% w/w |
|---|---|
| SIS/SI copolymer (Kraton 1163) | 10% w/w |
| Low molecular weight SI copolymer (LVSI) | 10% w/w |
| Tackifier, Arkon P90 | 10% w/w |
| Parafin oil, PL500 | 25% w/w |
| Blanose | 30% w/w |
| Aquasorb A800 | 5% w/w |

The SIS/SI copolymer, Polyisobutylene, LVSI and ⅓ of the oil was mixed in a Z-blade mixer at 140° C. The blend was mixed for 30 minutes to yield a homogeneous mass. The temperature was lowered to 120° C. over 20 minutes while the mass was still mixed. Tackifier and the remaining oil was added. Mixing continued for 20 min. The temperature was now again lowered to about 105° C. and the carboxy methyl cellulose was added and mixing was continued for approximately 15 min until the mass was homogeneous. About 1 kilo of adhesive was prepared in this way.

Step 2. Foaming

The adhesive was heated above its melting point to 120° C. and pumped to a static mixer using a gear pump. The gear pump raised the pressure of the adhesive to app. 50 bar while the temperature was kept constant at 120° C. Before reaching the static mixer, a measured amount of nitrogen gas was continuously added to the adhesive to create a mixture of gas and adhesive. Concentration fluctuations were reduced by allowing the mixture to flow through the static mixer. The pressure was then relieved over a valve. The mixture was feed through a die onto a release liner to produce an extruded adhesive film of 600 µm in thickness. Average bubble size was 50 µm with 95% of the bubbles in the range of 10-150 µm. The density of the adhesive was measured to be about 80% of the un-foamed adhesive.

Tests

Un-foamed incompressible adhesives plates of same thickness as in example 1 were produced for comparison. Both the compressible and incompressible adhesives were mounted on a polyurethane backing for peeling. Further, a hard tape was mounted on top of the PU film for the peeling experiment. For investigating the peel front a setup was constructed that made it possible to film the peel front in a microscope (see FIG. 1). The setup moves the substrate right with a velocity v. At the same time, the peeled adhesive is drawn to the left with the same velocity v, leaving the peel front area stationary. Peel angle is kept at 180° to mimic a typical peel situation. Through the microscope, the peel front is filmed and the broadness (l) of the peel front can be determined by observing the distance from the backing tape to the peelfront line. The broadness is normalized with the thickness of the adhesive to yield a dimensionless peel front broadness $b=(l-l_0)/l_0$.

Figure 2:
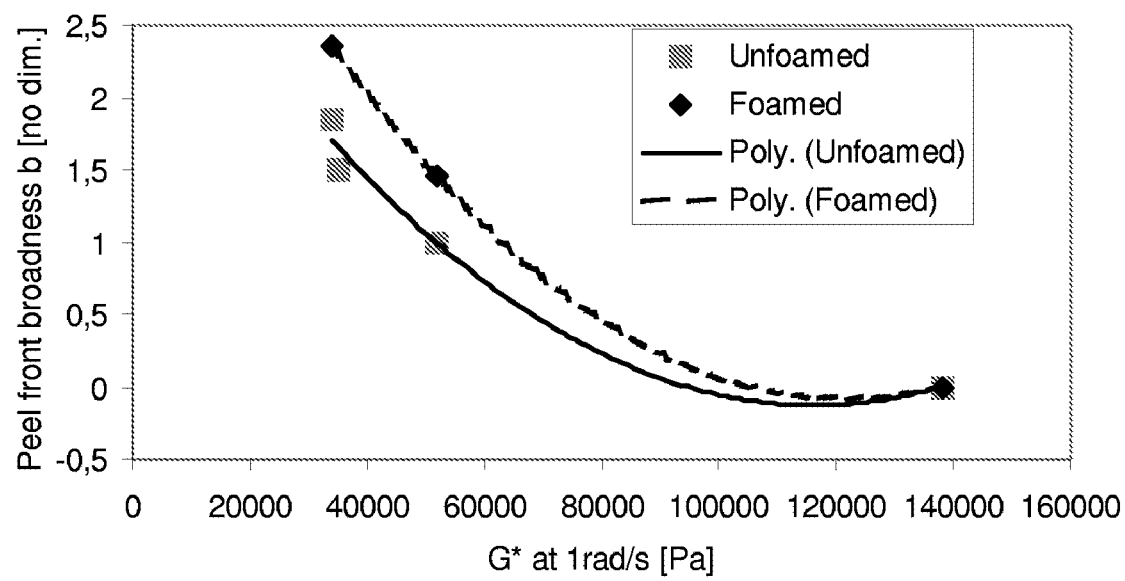
FIG. 2 shows a plot of peel front broadness versus adhesive hardness.

The peelfront broadness was now plotted as function of the adhesive tested. As a measure of adhesive hardness, we use $|G^*|$ at 1 rad/s measured in a plate-plate rheometer: A plate of the unfoamed material was pressed into a plate of 1 mm thickness. From this a round sample of 25 mm in diameter was cut out and placed in a RheoStress RS600 rheometer from Thermo Electron. The geometry applied was parallel plates 25 mm and deformation was fixed at 1% to ensure that measurements were in the linear regime. The measurement was carried out at 32° C. Peel broadness b for a range of foamed and un-foamed samples are plotted in FIG. 2. The values in FIG. 2 are measured at 180° peel angle.

Example 2

Measuring Stability of the Un-Foamed Adhesive

To test stability of foamed hydrocolloid adhesives, a number of foamed hydrocolloid adhesives were produced. Microscopy pictures were recorded after the foaming in such a way that the photographed area could be found again. The samples were stored at 40° C. for five days and pictures were recorded at the same place as earlier. Before and after pictures were now compared in terms of bubble stability. When 50% of the bubbles in the range from 50-100 µm remained stable in this interval after storage at 40° C. for 5 days, the foamed adhesive was considered stable. Experiments were performed with adhesives with different tan δ at 0.001 rad/s measured at 40° C. Results are tabulated in table 2.

TABLE 2

|  | Adh1 | Adh2 | Adh3 |
|---|---|---|---|
| SIS | 24.9% | 24.0% | 9.2% |
| LVSI |  |  | 9.2% |
| PIB |  |  | 9.2% |
| Aliphatic resin | 34.9% | 34.4% | 9.2% |
| Paraffin oil |  |  | 23.1% |
| DOA plasticizer | 8.7% | 5.0% |  |
| carboxymethyl cellulose | 30.3% | 20.0% | 40% |
| Potato starch |  | 16.6% |  |
| Antioxidant | 1.2% |  |  |
| Percentage stable bubbles | 0% | 18% | 59% |
| tan δ at ω = 0.001 rad/s and T = 40° C. | 1.6 | 0.65 | 0.27 |
| Stable | No | No | Yes |

The results show a clear connection between tan δ at 40° C. and 0.001 rad/s and stability of the bubbles in the foam. If we extrapolate Adh2 and Adh3 to 50% stable bubbles, we get a tan δ criterion of tan δ<0.35 at 40° C. and 0.001 rad/s for bubbles to be stable in a HC foamed HC adhesive.

Example 3

A thermosetting foamed pressure sensitive adhesive with hydrocolloids were produced.

Materials:

ACX003, allyl-terminated polyether (poly propylene oxide) viscosity 16 Pa·s from Kaneka.

Catalyst, Pt-VTS. Pt-VTS is Pt-divinyl teteramethyl disiloxane in IPA (Pt 3.0 wt %).

CR600, poly-alkyl hydrogen siloxane curing agents available from Kaneka.

Blanose (carboxymethyl cellulose) from Hercules containing about 2 wt % water.

TABLE 3

| Mixing ratios of PPO + HC adhesive base | |
|---|---|
| Polymer AC003 batch3076 | 67.5% |
| Cross linker CR600 | 2.4% |
| Catalyst | 0.1% |
| Blanose containing 2% water | 30% |

The ingredients were mixed in the specified ratios to yield a total of 20 g. This liquid mass was placed between two pieces of releaseliner and pressed at 110° C. At this temperature, the water flashed out of the hydrocolloid and formed small bubbles in the liquid. At the same time, the liquid cured and captured the small bubbles in the cured adhesive and thereby foaming the adhesive. Tan $\delta$=0.05 was measured for the adhesive at 0.001 rad/s and 40° C. Visual inspection after storage at 40° C. for 1 month revealed no loss of foam structure of the adhesive.

The invention claimed is:

1. An absorbent adhesive body of a foamed pressure sensitive hydrocolloid adhesive comprising one or more water soluble or water swellable hydrocolloids and having gas bubbles incorporated therein, gas in the gas bubbles being in direct contact with said pressure sensitive hydrocolloid adhesive, and tan $\delta$ for said adhesive in un-foamed form being below 0.35 at 40° C. and 0.001 rad/sec.

2. The absorbent adhesive body according to claim 1, wherein the average bubble diameter is between 20-80 μm.

3. The absorbent adhesive body according to claim 2, wherein the average bubble diameter is 30-70 μm.

4. The absorbent adhesive body according to claim 2, wherein at least 95% of the bubbles have a bubble diameter between 10 and 150 μm.

5. The absorbent adhesive body according to claim 1, wherein the un-foamed pressure sensitive hydrocolloid adhesive has a complex modulus below 80 kPa at 1 rad/s.

6. The absorbent adhesive body according to claim 1, wherein the density of the foamed pressure sensitive hydrocolloid adhesive is below 90% of the density of the same un-foamed adhesive.

7. The absorbent adhesive body according to claim 1, wherein more than 90% of the bubbles are closed celled.

8. The absorbent adhesive body according to claim 1, wherein the amount of hydrocolloid in the foamed pressure sensitive adhesive is above 20% w/w.

9. The absorbent adhesive body according to claim 8, wherein the foamed pressure sensitive hydrocolloid adhesive comprises a styrene block copolymer, a tackifier and one or more water soluble or water swellable hydrocolloids.

10. The absorbent adhesive body according to claim 9, wherein the foamed pressure sensitive adhesive comprises one or more polyisobutylenes and/or mineral oil.

11. The absorbent adhesive body according to claim 1, having a flat or curved first surface adapted to be attached to the skin.

12. The absorbent adhesive body according to claim 11, wherein the adhesive body is a layer of uniform thickness optionally with a bevelled peripheral portion, or the adhesive body is a layer, which is thickest in the central portion and gradually becomes thinner towards peripheral edge.

13. The absorbent adhesive body according to claim 12, wherein the average bubble diameter is below 25% of the thickness of the adhesive body where it is thinnest.

14. A dressing comprising an absorbent adhesive body according to claim 1, wherein the absorbent adhesive body has a surface adapted for being attached to the skin releasably attached to a release liner and another surface inseparably attached to a backing layer.

15. A dressing comprising: the absorbent adhesive body according to claim 1 as a cushioning element, and a backing film.

16. An ostomy appliance having a wafer or base plate, comprising: an absorbent adhesive body according to claim 1, and a collecting bag.

17. An incontinence device comprising: an absorbent adhesive body according to claim 1, and a urisheath.

18. A method for attaching an incontinence device to skin, which comprises securing the incontinence device to the skin with an adhesive body according to claim 1.

19. A method for sealing around a medical device attached to skin, which comprises attaching an adhesive body according to claim 1 to the medical device and the skin.

* * * * *